United States Patent [19]

Farmer

[11] 4,329,870
[45] May 18, 1982

[54] METHANE MONITOR SENSING SYSTEM

[76] Inventor: D. Eugene Farmer, P.O. Box 542, Mt. Gay, W. Va. 25637

[21] Appl. No.: 44,231

[22] Filed: May 31, 1979

[51] Int. Cl.³ ............................................. G01N 27/12
[52] U.S. Cl. ..................... 73/23; 339/91 R; 340/634
[58] Field of Search ................. 73/23, 27 R; 340/632, 340/634; 339/91 R

[56] References Cited

U.S. PATENT DOCUMENTS

| | | | |
|---|---|---|---|
| 1,451,979 | 4/1923 | Fenn | 339/91 R |
| 3,266,293 | 8/1966 | Hubner | 73/23 |
| 3,877,291 | 4/1975 | Hoppesch et al. | 340/634 |
| 3,879,717 | 4/1975 | Gruensfelder | 340/634 |

OTHER PUBLICATIONS

Figaro Engineering Report, Figaro Gas Sensor, pp. 1-5, 7, 10-16, Apr. 1975.
C. R. Lewart, "Build A Gas Sensor", Radio Electronics, vol. 47, No. 7, pp. 46-47, Jul. 1976.

*Primary Examiner*—Stephen A. Kreitman
*Attorney, Agent, or Firm*—Cushman, Darby & Cushman

[57] ABSTRACT

A methane monitor is disclosed that has at least one removable and replaceable sensor interchangeably inserted into a receptacle located on the outside wall of the monitor. A thumb operated latch attached to the sensor is used for connecting the sensor into the receptacle.

2 Claims, 4 Drawing Figures

METHANE MONITOR SENSING SYSTEM

This invention relates to part of a methane monitoring system used on mining equipment to prevent operation of the equipment in heavy concentration of methane gas. My invention has special reference to the part of the system that detects or senses the gas in the air of the mine.

The objects of this invention is to provide a better methane monitor sensor system providing a much quicker and easier replaced sensor by using a thumb-pressure operated latch with plug-in connections for electrical contact; also make troubleshooting the methane monitoring system easier by inserting a test circuit with an indicator light to show when the sensor is good or bad; and to cut down on down-time on a piece of mining equipment by having a built in spare sensor with quick and easy switching from one sensor to the other.

Other advantages and their adaptability to work on all monitoring system can be seen from examing the attached drawings in which.

Figure 1:
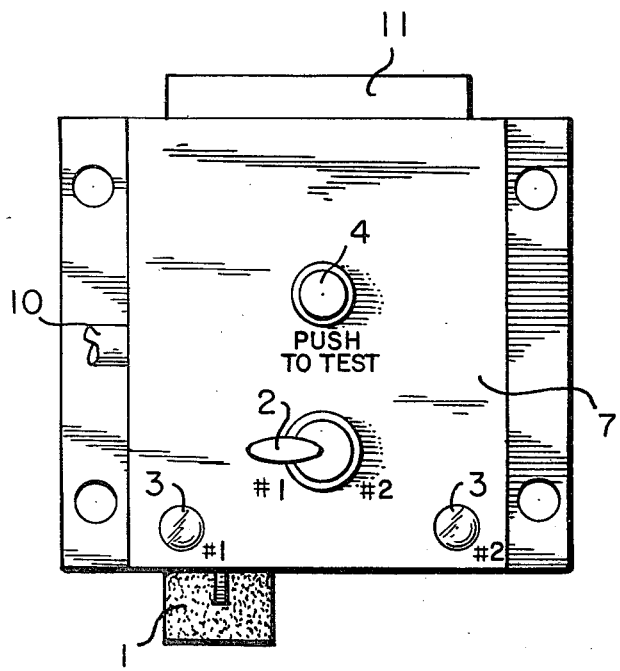
FIG. 1 is a top view of my sensor housing.
Figure 4:
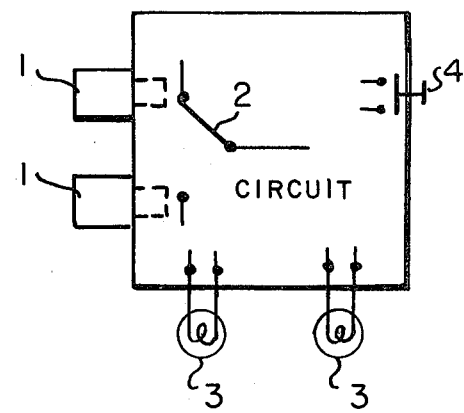
FIG. 4 is a schematic view including the circuit.
Figure 2:
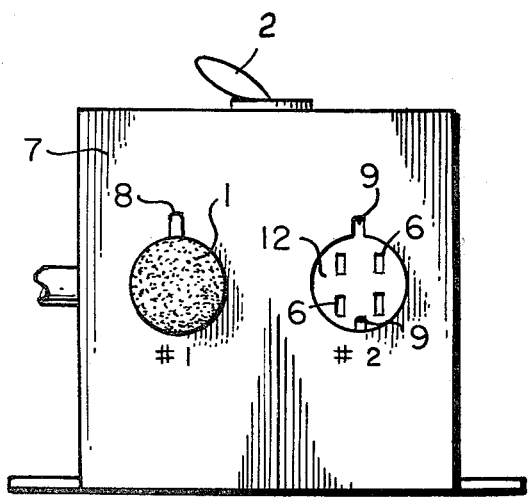
FIG. 2 is a front view of my sensor housing.
Figure 3:
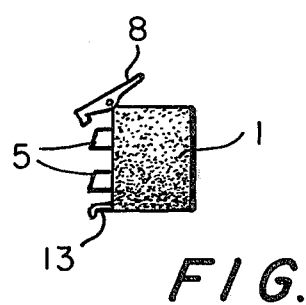
FIG. 3 is a side view of the sensor element used in my invention.

As shown in FIG. 1, FIG. 2 and FIG. 4, my methane sensor system has 2 complete and seperate methane sensors (1). Each of these has inside, a sensing element and a compensator element coming to contact with the male plugs (5). The female receptacle (12) is located in the sensor housing (7). This is held in by screws from inside of the housing (7). The sensor (1) is held into place by a spring-loaded latch (8). From FIG. 1 you can see two indicator lights (3) which are used to indicate a good or bad sensor when the test button (4) is pushed. The male contacts (5) on FIG. 3 are plugged into the female recetacle (12) and make electrical contacts through metal contacts (6). The sensor (1) is held into place by a hook (13) on the bottom which fits into the bottom slot (9). The top of the sensor (1) is held by a spring latch (8) which is thumb-operated. The entire unit is wired to the methane monitoring device by a cable (10). Access to the inside of the housing (7) is by a threaded lid (11).

As you can see from FIG. 2 and FIG. 3 the quick change sensor (1) will eliminate the job of taking the sensor housing apart to change sensors. When a bad sensor is detected it can be unplugged and another inserted into it's slot with very little trouble and a very short time. In the present monitors most sensor assemblies have to be removed from the machine to change the sensor elements.

Also you can see from FIG. 1, I have inserted a test button (4) which is wired so that when the button (4) is pushed in, the circuit to the wheatstone bridge, which all monitoring systems employ, is broken and the circuit current is directed through both sides of the sensing elements and through the indicator light bulb (3) or a LED can be used. Therefore when you have a good sensor with both elements conducting, the current will pass through them and the indicating lights (3), causing the lights to burn. But if either element is open the current cannot flow through the light thus the bulb will not burn indicating an open sensor. Because nearly all monitoring systems are different I cannot go into detail for each system, however the idea can be applied to all systems.

Also from FIG. 1 and FIG. 2 you can see I have incorporated a built in spare sensor (1) with a switch (2) to switch operation from one sensor to the other sensor. I have done this by simply taking a toggle switch with as many poles as needed (some are 3 wires some are 4 wires). The in coming wires from the cable (10) are wired to the common posts of the switch (2). One sensor (1) is wired to the normally opened side, the other hooked to the normally closed side of the switch. They are hooked so that #1 sensor is in operation when the toggle switch is pointed in the #1 position on the sensor housing as shown in FIG. 1.

I believe that this sensing system is superior to present models and I believe I have demonstrated this in this application.

I claim:

1. A monitor for the analysis of methane comprising at least one removable and replaceable methane sensor adapted to be inserted interchangeably into at least one receptacle located on the outside wall of the said monitor by plugs attached to said sensor, which enables said sensor to be connected to a circuit means having a switch means for connecting one of the said sensors at a time to the said circuit means that illuminates a designated bulb attached on the monitor when the said sensor is correctly operating, and with a thumb operated latch attached to said sensor for latching said sensor into any of the said receptacles.

2. A methane monitor as in claim 1 with at least one methane sensor as described herein that varies in its degree of sensitivity and can be interchangeably inserted into each and any said receptacle located on the outside wall of the said monitor.

* * * * *